(12) United States Patent
Walzman

(10) Patent No.: US 11,642,213 B2
(45) Date of Patent: May 9, 2023

(54) CAPED STENT

(71) Applicant: Daniel Ezra Walzman, Bergenfield, NJ (US)

(72) Inventor: Daniel Ezra Walzman, Bergenfield, NJ (US)

(\*) Notice: Subject to any disclaimer, the term of this patent is extended or adjusted under 35 U.S.C. 154(b) by 0 days.

(21) Appl. No.: 16/913,536

(22) Filed: Jun. 26, 2020

(65) Prior Publication Data

US 2020/0323620 A1 Oct. 15, 2020

Related U.S. Application Data

(60) Division of application No. 16/214,130, filed on Dec. 9, 2018, now Pat. No. 11,007,048, which is a continuation-in-part of application No. 15/732,544, filed on Nov. 22, 2017, now abandoned.

(60) Provisional application No. 62/497,851, filed on Dec. 5, 2016.

(51) Int. Cl.
*A61F 2/07* (2013.01)
*A61F 2/958* (2013.01)

(52) U.S. Cl.
CPC ............ *A61F 2/07* (2013.01); *A61F 2/958* (2013.01); *A61F 2002/077* (2013.01); *A61F 2210/0076* (2013.01)

(58) Field of Classification Search
CPC .............. A61F 2/07; A61F 2002/075; A61F 2002/077; A61F 2002/2852; A61F 2002/826; A61F 2/89; A61F 2/958; A61F 2210/0076
See application file for complete search history.

(56) References Cited

U.S. PATENT DOCUMENTS

| | | |
|---|---|---|
| 6,379,382 B1 | 4/2002 | Yang |
| 6,428,569 B1 | 8/2002 | Brown |
| 6,635,082 B1 | 10/2003 | Hossainy |
| 7,118,592 B1 | 10/2006 | Dang et al. |
| 8,343,204 B2 \* | 1/2013 | Osborne ............. A61F 2/07 623/1.11 |
| 8,398,701 B2 | 3/2013 | Berez |
| 10,327,790 B2 | 6/2019 | Garrison |
| 2001/0049554 A1 | 12/2001 | Ruiz |
| 2002/0121472 A1 | 9/2002 | Garner |
| 2003/0055452 A1 | 3/2003 | Joergensen |
| 2005/0027345 A1 | 2/2005 | Horan |
| 2005/0110214 A1 | 5/2005 | Shank et al. |

(Continued)

FOREIGN PATENT DOCUMENTS

WO WO 2005/112823 A1 12/2005

OTHER PUBLICATIONS

Chun Fang, et al., Using a covered stent for large cerebral aneurysms treated with stent-assisted coiling (Interv Neuroradiol. Jun. 2015; 21(3): 317-324).

(Continued)

*Primary Examiner* — Christopher D. Prone

(57) ABSTRACT

A stent body having a frame having a plurality of openings. A first cover overlies and is attached to the frame to cover a first portion of the frame and has a free floating end unattached to the frame. A second cover overlies and is attached to the frame to cover a second portion of the frame, the second cover having a free floating end unattached to the frame. The first cover overlaps a first region of the second cover.

23 Claims, 5 Drawing Sheets

(56) References Cited

U.S. PATENT DOCUMENTS

| | | |
|---|---|---|
| 2007/0219619 A1 | 9/2007 | Dieck et al. |
| 2008/0281394 A1 | 11/2008 | Jones |
| 2012/0259404 A1* | 10/2012 | Tieu .................. A61F 2/966 |
| | | 623/1.15 |
| 2012/0316632 A1 | 12/2012 | Gao |
| 2014/0025151 A1 | 1/2014 | Gao |
| 2019/0151072 A1 | 5/2019 | Walzman |
| 2020/0323620 A1 | 10/2020 | Walzman |

OTHER PUBLICATIONS

Shogo Nishi, et al., Treatment of rabbit carotid aneurysms by hybrid stents (microporous thin polyuerethane-covered stents): Preservation of side-branches (J Biomater Appl. 2014).
PCT/US2022/012083 International Search Report And Written Opinion (dated Mar. 30, 2022).

* cited by examiner

CAPED STENT

CROSS-REFERENCE(S)

This application is a divisional of U.S. application Ser. No. 16/214,130, filed on Dec. 9, 2018, now U.S. Pat. No. 11,007,048, which is a continuation-in-part of U.S. application Ser. No. 15/732,544, filed Nov. 22, 2017 (22 Nov. 2017), which claims priority from provisional Ser. No. 62/497,851 filed Dec. 5, 2016 (5 Dec. 2016). The entire contents of each of these applications are incorporated herein by reference.

FIELD OF THE INVENTION

The present disclosure relates to medical devices used to treat aneurysms and fistulas within unhealthy blood vessels, and more particularly, relates to endovascular devices.

BACKGROUND OF THE INVENTION

Prior Art

The prior art teaches the use of a number of devices to treat aneurysms. A common blood vessel difficulty is the persistent blood flow in the aneurysm sac extrinsic to the endograft. In fact, this is the most common complication after endovascular aneurysm repair (EVAR). Such endoleaks are ameliorated by a number of means. For example, Walzman's utility application Ser. Nos. 15/732,147 and 15/732,365 teach the use of hydrogel to prevent endoleaks.

The prior art also teaches endovascular coiling as a minimally invasive technique performed to prevent blood from flowing into some saccular aneurysms. This treatment results in the coil inducing embolization (clotting) of the aneurysm, which prevents blood from flowing into the aneurysm, which in turn, prevents rupture and subsequent subarachnoid hemorrhage. Endovascular coiling however may result in procedural complications include thromboembolism, cerebral embolization, aneurysm perforation, parent artery occlusion, coil migration, arterial dissection, and others. The prior art also teaches stent-assisted coiling. The stent-assisted coiling also has some of the same short comings related to stent placement and placing a stent in the parent artery requires prolonged use of anti-platelet agents to reduce the risk of thrombosis-based stenosis within the stent.

Some aneurysms and fistulas are ideally treated with covered stents, which can most directly cover the hole of the fistula or the neck of the aneurysm and reconstruct the vessel wall, immediately redirecting blood flow into the normal path of the parent vessel. However, there is no covered neuro-stent currently available in the United States. The U.S. Food and Drug Administration (FDA) has examined and tested such covered neuro-stents but none has "FDA approval," which means that the FDA has not decided the benefits of the previous versions of covered neuro-stents outweigh the potential risks for the item's planned use. Additionally, there are currently no covered stents that are effective in severely tortuous anatomy in other parts of the body, including but not limited to splenic artery aneurysms and pulmonary arteriovenous fistulas.

A potentially significant use of covered neuro-stents is for the treatment of fistulas, particularly for Carotid cavernous fistula (CCF) which is an abnormal communication between the cavernous sinus and the carotid arterial system.

Other treatment of aneurysms includes surgical clipping of an intracranial aneurysm, which involves the application of a clip across the neck of the aneurysm. This treatment has several shortcomings including that it requires an open operation and physical manipulation of the brain. Sometimes surgical bypass is considered as well, but typically is associated with even higher rates of morbidity and mortality.

Additionally, prior art teaches the use of flow diversion devices to divert flow away from the aneurysm by placing a mesh stent or a structure similar to a stent, on the aneurysm neck along the parent artery. The use of these devices allows for thrombus formation inside the aneurysm. However, increased technical complications can develop following the deployment of flow diverters. Additionally, because they do not completely block flow, they are not effective in the treatment of fistulas and ruptured vessel. Similarly, there is currently no effective vessel-sparing treatment of an iatrogenic rupture of an intracranial artery. Current treatment requires closing the ruptured artery with coils and/or liquid embolics to stop the bleeding, usually with significant resulting morbidity from ischemic injury to that arterial territory. Furthermore, when treating aneurysms with these devices, the aneurysm thromboses over time, a lag period, and is not immediately cured. This leaves the patient at risk of aneurysmal rupture during lag period. This can be especially problematic when treating ruptured aneurysms, which have high short-term re-rupture rates.

A need exists for an endovascular device capable of endovascular intervention for immediate cure of select intravascular aneurysm or fistula, while ameliorating the difficulties and shortcomings associated with the currently available technologies. More particularly, a need exists for a covered stent which allow said stent freedom of motion and bending without kinking around tight bends in tortuous anatomy.

Most covered stents involve producing a cylinder of a stent "skeleton" or "frame" out of semirigid materials such as metal alloys, and then attaching an impermeable "cover" to said frame. The prior art teaches such attachments are diffuse and located throughout the covering of a stent, along fixed intervals of said covering and frame, and consequently significantly limit flexibility of the device. The present invention teaches a covered stent device capable of safe and effective delivery and deployment into tortuous vessels to effectively diverting blood flow away from an aneurysm, fistula, or ruptured vessel while allowing blood to flow to healthy tissue distal to the targeted treatment area and still resulting in blood stasis and thrombus formation inside the aneurysm or fistula. Thus, a need exists for a covered neuro stent as well as a covered stent which is capable of use in other tortuous anatomy outside of brain. The present invention satisfies this need.

SUMMARY OF THE INVENTION

The present invention is a stent with a free-floating cover. Said floating cover is designed to optimize insertion in tortuous anatomy. Among its unique structural elements are a single circumferential attachment point at one end (as small as 1 nm), overlapping circumferential shingles and overlapping geometric shingles.

In one embodiment, said geometric shingles are triangles attached on one end. Said shingles would overlap like scales on a fish.

Such single circumferential or longitudinal attachment point optionally combined with said overlapping circumferential shingles allow the present invention to bend without kinking. This feature will allow sufficient flexibility to warrant its use as a covered neuro stent as well as to be useful in other tortuous anatomy outside of brain as well.

In other embodiments, said overlapping geometric shingles may have attachment to said frame on only one side, comprising less than 70% of the length of said shingles, with said shingle optionally being attached only along a limited segment of the circumference or longitudinal surface of said frame, with additional overlapping shingles and their independent attachments extending over a covered segment or segments of the stent, thus resulting in complete coverage of said segment(s) of the stent.

The disclosed device may optionally be deployed under flow arrest, via pharmacologic means, or via delivery through a balloon guide catheter with temporary balloon inflation or other means, to minimize the possibility of blood flow folding or bunching the fabric as it is unsheathed.

In still other embodiments, said coverings may not fully encircle a given segment of said frame, thus allowing some stents to be covered along a portion of its circumference while being uncovered at a different circumferential side of the same segment. This can sometimes allow preservation of the origin of a branch vessel that might arise from the parent vessel along the same segment of said parent vessel; for example, opposite to a fistula or the neck of an aneurysm.

DETAILED DESCRIPTION OF THE INVENTION

Figure 1:
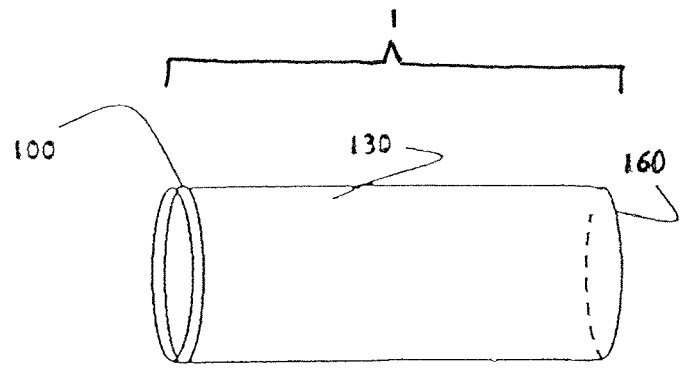
FIG. 1 shows the cape element 1 of the present invention, having an impermeable seal element 130, cape attachment element 100, and a free end 160.
Figure 2:
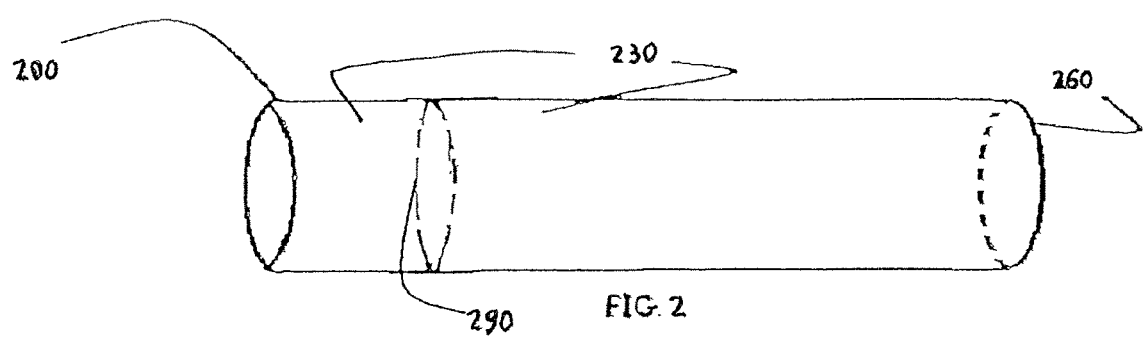
FIG. 2 depicts a translucent, permeable stent 230 element, having a first end 200, a second end 260, and stent attachment element 290; the permeable mesh is not shown (to highlight attachment element 290).
Figure 3:
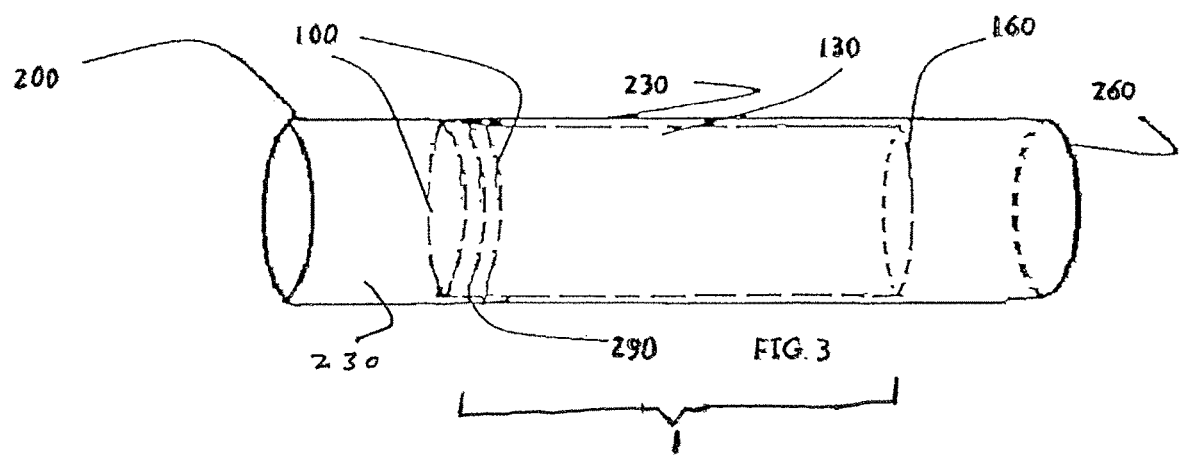
FIG. 3 shows the cape element 1 of FIG. 1 attached where stent element 290 meets cape element 100.
Figure 4:
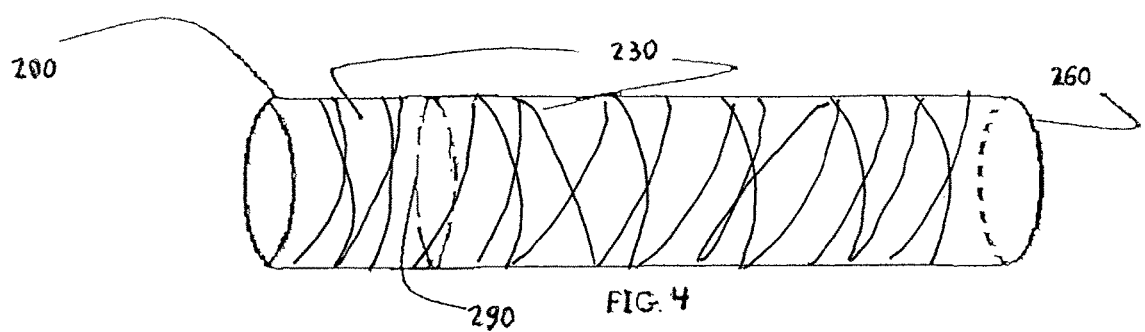
FIG. 4 shows the stent element 230 of FIG. 2, substituting wire struts for a stent mesh with small permeable openings.
Figure 5:
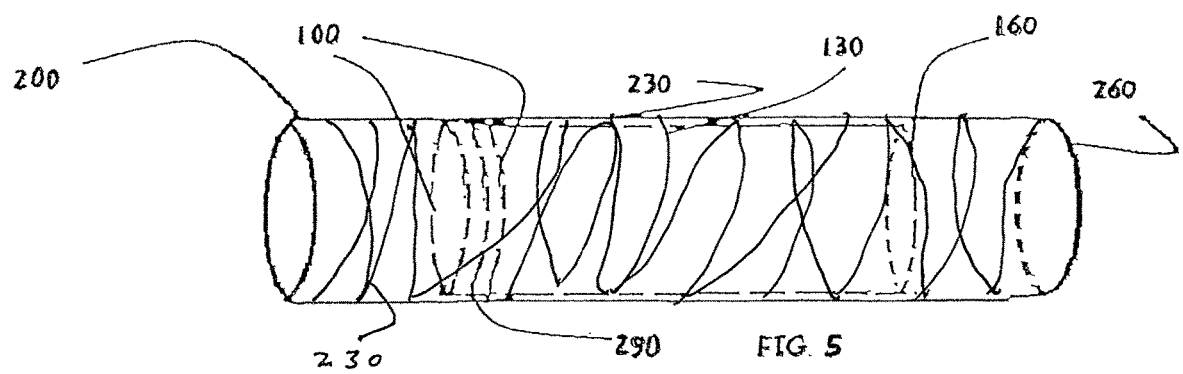
FIG. 5 shows the same elements as FIG. 3, substituting wire struts for a stent mesh with small permeable openings.

Referring now to FIGS. 1-3, in a preferred embodiment, seal element 130 is attached to a stent body 230 by connection element 100 on cape element 1 to attachment element 295 on stent 230. Seal element 130 varies in length (from connector 100 to free end 160) according to the size of the target vessel. The seal 130 should be approximately 30% longer than the area of the target vessel intended to be covered in order to prevent rigidity at bends. More particularly, insofar as the cover 130 is only attached to stent 230 outside the seal-deployment area, the stent 230 will be more flexible than a stent having a cover attached throughout.

An advantage of the current invention is that stent 230 is allowed to move at sharper angles than covered stents of the prior art. This feature means that the current invention presents no sharp edges which can lead to abrasion, puncture, rupture or other damage to the target vessel while allowing better conformance to the vessel wall in addition to a continuous seal. The cape design of the current invention eliminates, or at least ameliorates, rigidity associated with covered stents by allowing free movement of the cape-cover 1. This feature allows the user easier deployment of the current invention than existing covered stents because the prior art forces the covering to distend when bent, thus increasing stiffness.

In an alternate embodiment the cylinder of fabric is on the outside of the skeleton of stent 230. The preferred embodiment has this configuration, with the attachment on the distal end (spanning a punctate/very short distance) of the covered zone. The covering can cover anywhere from 1% to 100% of the stent. In the preferred embodiment it covers the central or medial portion of the stent 230 skeleton while leaving the first end 200 and second end 260 of the skeleton uncovered. In the preferred version the attachment zone is circumferentially around the stent in a distal position, making delivery easier. However, it can be proximal as well. This design results in covered stents which can more freely bend along the contour of tortuous vessels, without kinking or straightening the vessel, compared to prior stents that had multiple or diffuse attachments between the "fabric" and the skeleton. The outer end of any curve requires a larger radius than the inner curve and the diffuse attachments of a typical covered stent require a fixed amount of fabric per interstices or zone of the stent, thus making the more usual configuration much more stiff.

The device of the present invention is deployed using a microcatheter or sheath (not shown). It may be deployed either out an end hole or side hole thereon. The present invention may be deployed via a balloon or wire.

The present invention may attach cape 1 to stent 230 either toward the distal end of stent 230 or the proximal end of stent 230. When stent 230 is deployed using a balloon (not shown) to activate the present invention, then the preferred embodiment is to attach cape 1 toward the proximal end of stent 230 because the balloon pushes the present invention open. When stent 230 is deployed using a wire (not shown) to activate the present invention, then the preferred embodiment is to attach cape 1 toward the distal end of stent 230 because the wire pulls.

In one embodiment of the present invention a separate stent 230 skeleton with an attached inner cylinder of covering "fabric" such as nylon, Dacron, pericardium, polyester, PET, PTFE or any other nonporous or minimally porous material, wherein the inner cylinder of fabric is only attached on one side, such as the distal end of the fabric or the proximal end of the fabric, to the skeleton. The attachment zone can be from as small as a punctate point circumferentially around the stent, to as much as 70%. In the preferred version the attachment point 135 would be very short. In the preferred version the "fabric" layer is outside the "frame/skeleton" layer. Alternatively, the "fabric" layer can be on the inside.

Figure 6:
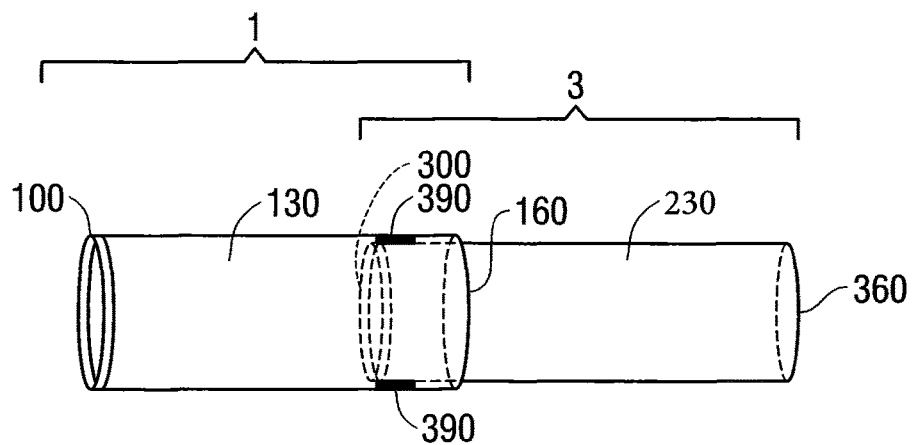
FIG. 6 shows how a first caped element 1 and a second caped element 3 are joined where telescope attachment element 390 located on cape element 1 between cape attachment element 100 and free end 160 meets attachment element 300 located on cape element 3.
Figure 7:
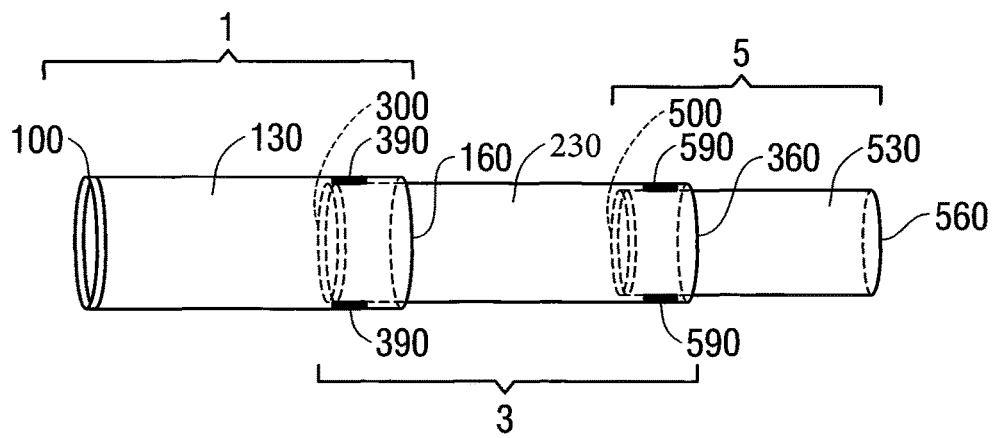
FIG. 7 shows how three caped elements are coupled. In particular, a first cape element 1, a second caped element 3 and a third cape element 5 are joined. Cape elements 1 and 3 are joined as described in FIG. 6 above. Second caped element 3 and a third cape element 5 are joined where telescope attachment element 590 located on cape element 3 in between cape attachment element 300 and free end 360, and meets telescope attachment element 500 located on cape element 5.
Figure 8:
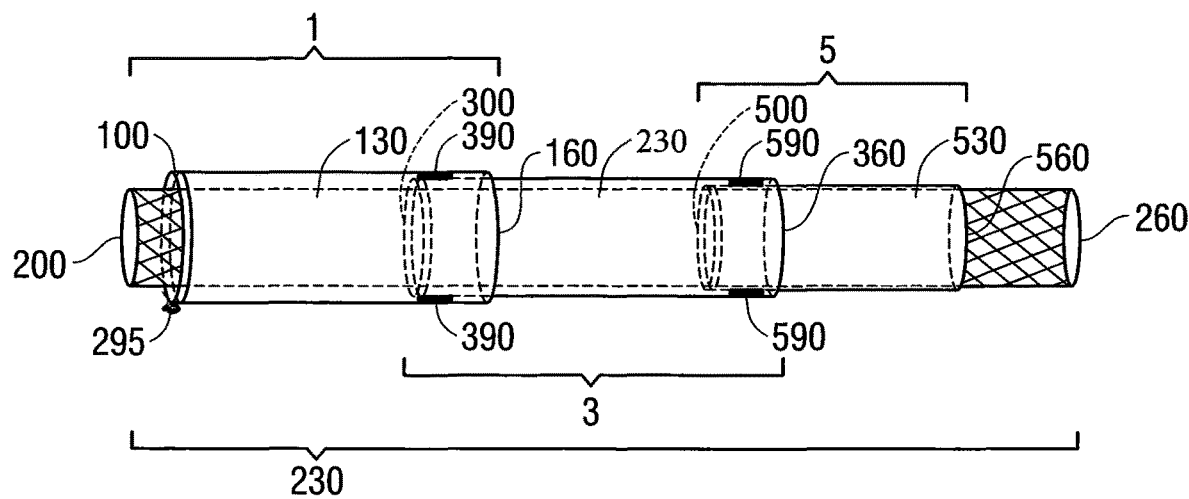
FIG. 8 shows all the elements of FIG. 7 with stent 230 passing through it. All caped elements are attached to stent 230 at a single point attachment 295. Additionally, element 100 of first caped element 1 fixes first cape element 2 to the stent at attachment element 295, located on stent 230 between first end 200 and second end 260.
Figure 9:
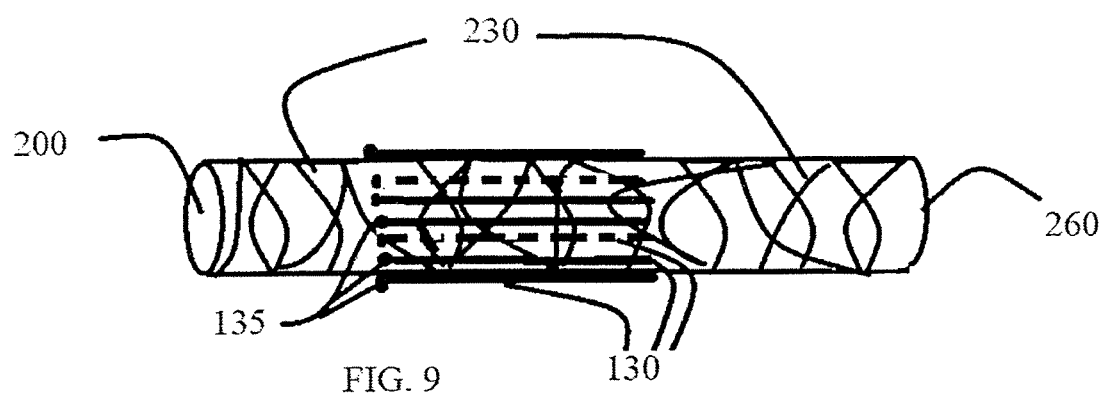
FIG. 9 is a side view of an alternate embodiment of a set of undeployed seal elements 130 joined at linear connection points 135 on the outer surface of stent 230 in the linear axis.
Figure 10:
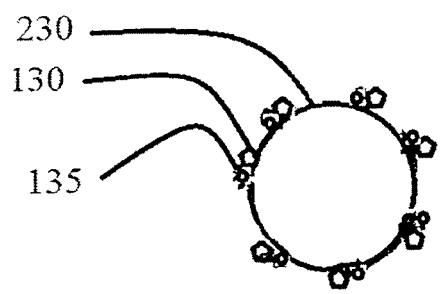
FIG. 10 is a top view from first end 200 of the undeployed stent 230 of FIG. 9, showing coiled seal elements 130 adjacent to connection points 135 attached to stent 230 disposed on the outer surface in the linear axis
Figure 11:
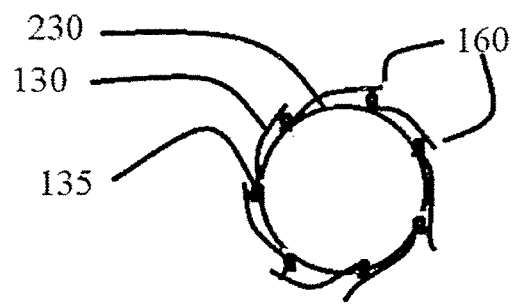
FIG. 11 depicts stent 230 of FIG. 10 in a deployed state, showing a plurality of unrolled seal elements 130 with each free end 160 making a flap over the first end 100 at the adjacent linear connection points 135 to form a fanfold-type overlap covering stent 230.
Figure 12:
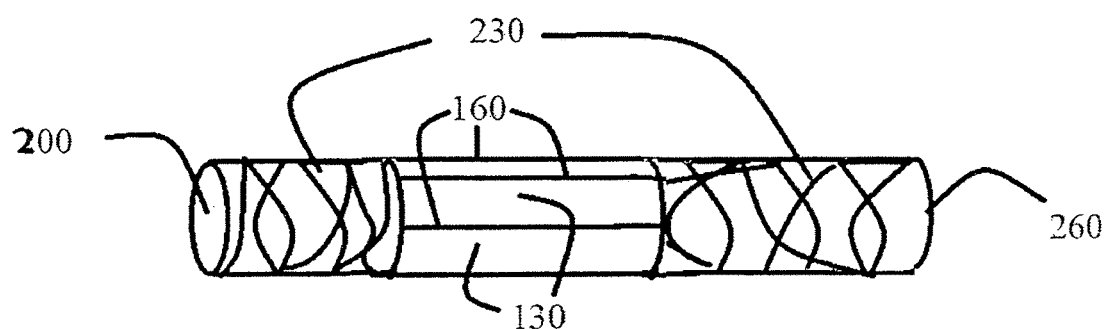
FIG. 12 is a side view of the embodiment of FIG. 9 in a deployed state, showing unrolled seal elements 130 forming a coverage band of overlapping free ends 160 about the medial circumference of stent 230.

Referring now to FIGS. 6-8 disclosing the overlap in between coverings, cover 1 overlaps 3, and 3 overlaps 5 by way of illustration to create an impermeable shingling effect. Said shingling effect is a significant improvement over prior art covered stents because each cape (1, 2 or 3) may be deployed completely without fully deploying other capes. The advantage is that a fistula may be covered without fully deploying the entire covered stent. Another advantage of this feature is that the present invention ameliorates the need for different-sized covered stents.

Figure 13:
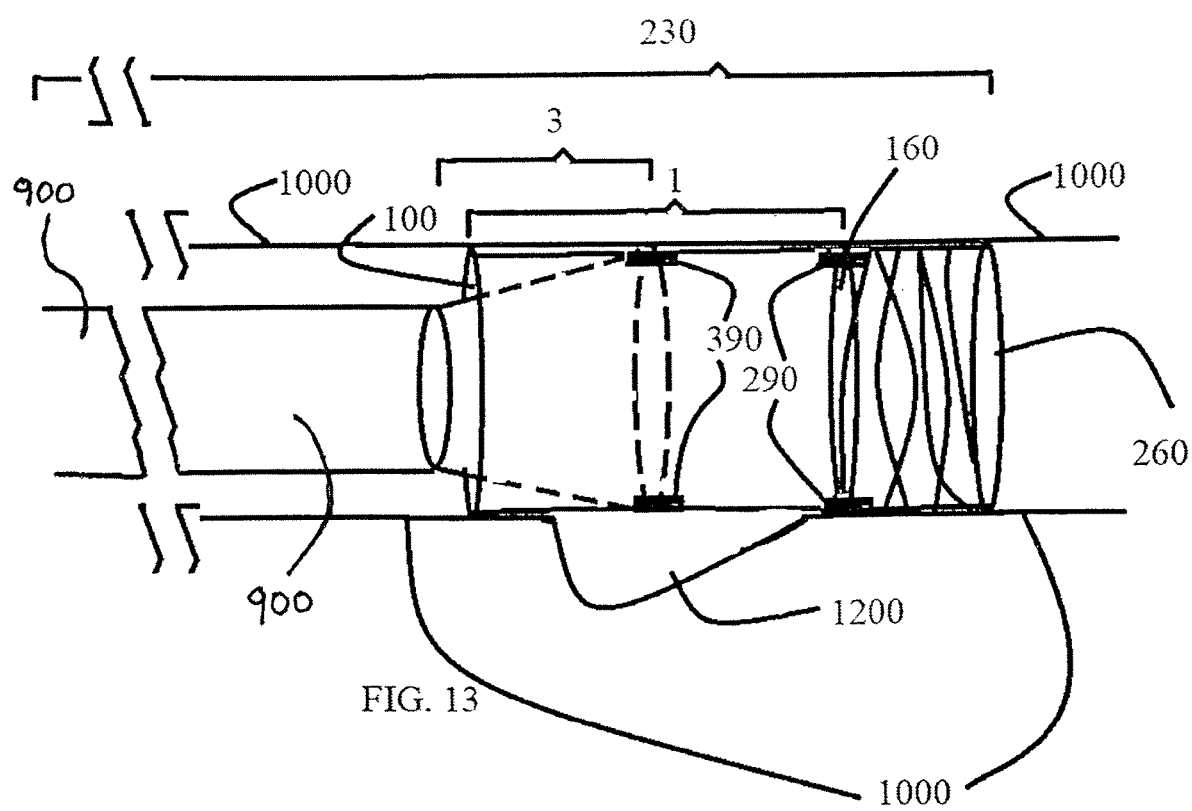
FIG. 13 is a side view of a self-expanding stent body in the process of deployment by delivery device 900 within target vessel 1000, wherein cape 1 is fully deployed, illustrating that fistula 1200 is covered prior to full deployment of cape 3.

Now referring to FIG. 13, which depicts the present invention covering a fistula without being fully deployed.

Referring now to FIGS. 9-12, in alternative embodiments the covered stents 230 instead of having a single continuous sheet there are multiple circumferentially 'shingled' sheets 1 of fabric, wherein the nonattached or free segment 160 of sealing fabric 130 from one sheet overlaps with the attached segment of the next sheet. This shingling allows the stent to more freely bend in zones where there is no attachment. The shingles can be on the inner surface or outer surface of the stent 230 skeleton or scaffold.

In yet another embodiment of the present invention the "fabric" is circumferential inside (not shown) or outside the skeleton, and has multiple intermittent circumferential attachment points 135 to the skeleton 230, but has excess length of "fabric" at free end 160 compared to "frame/skeleton" at the optimal diameter in each segment between the attachments, to allow the skeleton to bend freely without being restricted by the fabric (the extra fabric will allow relative lengthening of the skeleton on the outer side of bends in the anatomy).

In a final embodiment of the present invention a similar shingling is used as in the foregoing embodiment, but the shingled capes 1, 2 or 3 comprise various geometric shapes that are not necessarily circumferential around the entire stent. Nonlimiting examples multiple triangles, wherein the covered segment has shingling that will effectively entirely cover the "covered" zone. Again, the shingled coverings can be disposed upon the inner surface or outer surface of the skeleton.

All embodiments can optionally have at least one uncovered opening in the covered.

All embodiments can optionally have multiple covered zones.

All embodiments can optionally have multiple uncovered zones.

The embodiments of the present invention may be a second telescoping stent, either on the inside for versions that have the "fabric" on the inside or on the outside for versions that have the fabric on the exterior of the skeleton, that can be used to pin the fabric between the two layers of skeleton. The second telescoping stent can either be a second built-in layer with the fabric layer sandwiched in between (but the fabric mostly unattached), or in the preferred embodiment of this optional additional stent layer it is placed separately as a separate, non-attached layer/device. This second skeleton can often minimize the risk of endoleaks at the non-attached regions. Endoleaks can be minimized where the "fabric" layer is not fully attached, if a second stent does not pin the "fabric" to the first then some of the fabric layers may have some freedom of movement—especially in regions where they are covering and aneurysm or a fistulous hole and not pinned fully to a vessel wall—and when they have some freedom of motion after implanted, blood flow can potentially sometimes flap them open, especially in the "shingled" version.

The present invention optionally includes an additional structure to minimize endoleaks. In particular each embodiment may have optional adhered hydrogel.

The "skeletons" of all embodiments of the present invention are composed of semi-rigid but flexible materials, such as metal alloys (containing chromium cobalt, and/or platinum, and/or nickel, titanium, steel, etc.) or synthetic fibers such as vicryl.

All elements of the present invention may be biodegradable or nondegradable. Alternatively, the present invention may be composed of both biodegradable or nondegradable elements. Element being complete components of a particular part of the present invention or sub-components of each part.

The present invention may employ self-expanding components.

The present invention may employ balloon-expanding components.

The present invention may optionally contain radiopaque components and/or radiopaque markers. These can be especially valuable at ends of stent and at the ends of covered zone. Radio-opaque materials and markers can also be optionally present in more places, and sometimes throughout.

The present invention's overlapping, underlapping, and/or shingled "fabric" layers may optionally have an additional "frame/skeleton" lattice supporting it, wherein that skeleton/frame is primarily supporting that "fabric" layer, and is an independent (but attached) skeleton layer to the main skeleton cylinder of the stent. For example, if there are triangular shingles of "fabric" attached on one end of the triangles to the outside of a metal skeleton/cylinder, each triangle of "fabric" may optionally have additional metal struts supporting it, provided such a skeleton is primarily free from the main cylinder (i.e.—no more than 70% of the support skeleton for unattached portion of the "fabric" is attached to the main skeleton stent/cylinder).

The present invention may have branched stent elements.

The present invention's stent elements may optionally be fully re-sheathable.

The present invention's stent elements may optionally be partly re-sheathable

All stent elements of the present invention may be optionally be detachable.

It should be noted that one representative example of a "Skeleton" and "fabric" layer, before their attachment (attachment in manufacturing process) attachment length (relative to "fabric") can be as small as 0.00001% and as much as 70%.

In this embodiment, the fabric is preferably attached at a distally punctate location such that it covers the skeletal surface. In a preferred embodiment the fabric is attached upon the outside of the skeleton such that it will contact the vascular walls upon deployment. The fabric uncoils together with the skeleton upon deployment. In an alternate embodiment, the fabric is attached on the interior surface such that it is disposed within the stent skeleton. In this configuration, the skeletal surface abuts the vessel wall.

The degree of overlap varies depending upon the diameter of the expanded stent skeleton and the lumen within which it is deployed. For example, in a 2 mm vessel, a 6 mm stent has an overlap of approximately two-thirds, whereas a 4 mm stent overlaps about two-fifths; in a 4 mm vessel the 6 mm stent overlaps about a third, and the 4 mm stent only about ²⁄₂₅ths (8%).

For clarity, the overlap of a coil-type stent skeleton is different from the optional embodiment of overlapping fabric capes (or covers) as described hereinabove. Overlapping stents overlap longitudinally, in the manner of fanfold or unrolled map. Overlapping capes or covers overlap in a telescoping manner.

In still another embodiment (not shown) the stent skeleton is a semi-cylindrical, having a discontinuous diameter and longitudinal edges overlapping in a loose coil in an undeployed state. The stent unrolls into an overlapping but substantially cylindrical shape as the skeleton expands when inserted in a target vessel. In such stent configurations, the cape of the current invention will be attached longitudinally.

It will be understood by those skilled in the art that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. An intravascular stent comprising:
   a) a single uncovered inner stent body having a frame, the frame having a longitudinal axis and a plurality of openings and an outer frame surface;
   b) a first outermost cover having an inner cover surface overlying and attached to the outer frame surface to cover a first portion of the frame and extending longitudinally over the first portion of the frame, the first cover having a first region, a second region and a free floating end unattached to the frame and made of a different material than the frame;
   c) a second outermost cover having an inner surface overlying and attached to the first cover to cover a second portion of the frame, the second cover having a first region, a second region and a free floating end unattached to the frame and unattached to the first cover and made of a different material than the frame;
   d) wherein the second portion of the frame is axially spaced from the first portion of the frame and a second region of the first cover overlaps a first region of the second cover; and
   e) wherein the stent is inserted into a vessel with the first cover attached to the frame;
   f) wherein the intravascular stent has a single stent body and the first and second outermost cover overly the outer frame surface of the stent body.

2. The intravascular stent according to claim 1, wherein the first cover overlaps the second cover at an attachment segment of the second cover.

3. The intravascular stent according to claim 1, wherein the first cover overlaps a portion of the second cover such that a majority of the second cover is not overlapped by the first cover.

4. The intravascular stent according to claim 1, wherein a terminal end of the free ends of the first and second covers are axially spaced.

5. The intravascular stent according to claim 1, wherein the first and second covers are each attached circumferentially to spaced external portions of the stent body.

6. The intravascular stent according to claim 1, wherein a terminal end of the stent body is not covered.

7. An intravascular stent comprising:
   a) a single uncovered inner stent body having a frame, the frame having a longitudinal axis and a plurality of openings and an outer frame surface;
   b) a first outermost cover having an inner cover surface overlying and attached to the outer frame surface to cover a first segment of the frame and extending longitudinally over the first segment of the frame, the first cover having a first region and a second region; and
   c) a second outermost cover having an inner surface overlying and attached to the first cover to cover a second segment of the frame, said second cover having a first region and a second region, the second cover expandable independent of the first cover;
   d) wherein the second segment of the frame is axially spaced from the first segment of the outer frame surface and the second region of the first cover overlaps a first region of the second cover such that a free end of the second cover is not overlapped by the first cover and is unattached to the first cover;
   f) wherein the intravascular stent has a single stent body and the first and second outermost cover overly the outer frame surface of the stent body.

8. The intravascular stent according to claim 7, wherein the first cover and second cover are expandable independent of the frame.

9. The intravascular stent according to claim 7, wherein the first cover overlaps the second cover at an attachment segment of said second cover along the stent body.

10. The intravascular stent according to claim 7, wherein the first cover overlaps a portion of the second cover such that a majority of the second cover is not overlapped by the first cover.

11. The intravascular stent according to claim 7, wherein the first and second covers are contiguous with the frame.

12. The intravascular stent according to claim 7, wherein a majority of each of the first and second covers are free floating.

13. The intravascular stent according to claim 7, wherein the first cover is attached to the stent body and the second cover is attached to the first cover prior to insertion of the stent and placement of the stent within the vessel.

14. The intravascular stent according to claim 7, further comprising a third cover expandable independent of the first and second covers, and the second and third covers partially overlap.

15. The intravascular stent according to claim 7, wherein a terminal end of the stent body is not covered.

16. An intravascular stent comprising:
   a) a single inner stent body having a first portion, a second portion, a longitudinal axis; a plurality of openings, an uncovered outer frame surface and an inner frame surface;
   b) a first outermost cover extending longitudinally and having an inner cover surface overlying and attached to the first portion of the stent body to form a first outer cover, the first cover having a first region and a second region; and
   c) a second outermost cover extending longitudinally and having an inner surface overlying and attached to the first cover to cover the second portion of the stent body to form a second outer cover, the second cover having a first region and a second region;
   d) wherein the second region of the first cover overlaps the first region of the second cover and an end of the first region of the second cover is not overlapped by the first and is free floating and is unattached to the first cover and unattached to the stent body;
   e) wherein the intravascular stent has an insertion condition and a placement condition, and the first cover is attached to the stent body in the insertion condition and in the placement condition;
   f) wherein the intravascular stent has a single stent body and the first and second outermost covers overly the outer frame surface of the stent body.

17. The intravascular stent according to claim 16, wherein the first cover overlaps the second cover at an attachment region of the second cover.

18. The intravascular stent according to claim 16, wherein the first cover overlaps only a portion of the second cover.

19. The intravascular stent according to claim 16, wherein the first cover covers a first longitudinal segment of the stent body and the second cover covers an adjacent second longitudinal segment of the stent body.

20. The intravascular stent according to claim 16, wherein each of the first and second covers combined extend over less than an entire length of the stent body.

21. The intravascular stent according to claim 16, wherein the stent body is made of a different material than the first cover and the second cover.

22. The intravascular stent according to claim 16, wherein except for the region where the first and second covers overlap, the outer layer of the stent is a single layer.

23. The intravascular stent according to claim 16, wherein a terminal end of the stent body is not covered.

* * * * *